(12) United States Patent
Bernstein

(10) Patent No.: US 9,801,563 B2
(45) Date of Patent: Oct. 31, 2017

(54) MICRO-MAGNETIC REPORTER AND SYSTEMS

(71) Applicant: The Charles Stark Draper Laboratory, Inc., Cambridge, MA (US)

(72) Inventor: Jonathan J. Bernstein, Medfield, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 499 days.

(21) Appl. No.: 14/533,661

(22) Filed: Nov. 5, 2014

(65) Prior Publication Data
US 2015/0126829 A1 May 7, 2015

Related U.S. Application Data

(60) Provisional application No. 61/900,692, filed on Nov. 6, 2013.

(51) Int. Cl.
*A61B 5/05* (2006.01)
*A61B 5/0478* (2006.01)
*A61B 5/04* (2006.01)
*A61B 5/00* (2006.01)

(52) U.S. Cl.
CPC .......... *A61B 5/05* (2013.01); *A61B 5/04008* (2013.01); *A61B 5/0478* (2013.01); *A61B 5/6868* (2013.01); *A61B 5/6869* (2013.01); *A61B 5/6877* (2013.01); *A61B 2503/42* (2013.01)

(58) Field of Classification Search
CPC ....... A61B 5/05; A61B 5/6868; A61B 5/6869; A61B 5/6877; A61B 5/0478; A61B 2503/42
See application file for complete search history.

(56) References Cited

U.S. PATENT DOCUMENTS

| | | | | |
|---|---|---|---|---|
| 4,026,276 A | * | 5/1977 | Chubbuck | A61B 5/0031 600/407 |
| 4,340,038 A | * | 7/1982 | McKean | A61B 5/031 219/635 |
| 4,608,992 A | * | 9/1986 | Hakim | A61B 5/031 600/431 |

(Continued)

OTHER PUBLICATIONS

Bernstein, Jonathan J., et al., Scanning OCT Endoscope with 2-Axis Magnetic Micromirror, Endoscopic Microscopy II, Proc. of SPIE, vol. 6432, 12 pages (2007).

(Continued)

*Primary Examiner* — Meredith Weare
(74) *Attorney, Agent, or Firm* — Hamilton, Brook, Smith & Reynolds, P.C.

(57) ABSTRACT

The present disclosure describes system and methods for detecting and amplifying weak magnetic fields generated by anatomical structures. The disclosure describes an implantable magnetic reporter system. The magnetic reporter system includes a magnetic reporter. The magnetic reporter includes a platform coupled to a support structure by a plurality of torsional flexures. A magnet is disposed on the platform, and the magnet and platform rotate when exposed to a magnetic field. The rotation of the magnet generates a stronger magnet field that is detectable external to the patient.

17 Claims, 4 Drawing Sheets

(56) References Cited

U.S. PATENT DOCUMENTS

| | | | |
|---|---|---|---|
| 6,681,131 B2 * | 1/2004 | Kandori | A61B 5/04007 324/244 |
| 6,714,336 B2 * | 3/2004 | Orcutt | G02B 6/359 359/225.1 |
| 7,252,634 B2 * | 8/2007 | Mizumo | A61B 1/00009 359/202.1 |
| 7,643,196 B2 * | 1/2010 | Bernstein | G02B 7/1821 310/40 R |
| 9,337,711 B2 * | 5/2016 | Hino | G02B 26/085 |
| 9,517,083 B2 * | 12/2016 | Sherry | A61B 17/3478 |
| 2002/0062076 A1 * | 5/2002 | Kandori | A61B 5/04007 600/409 |
| 2003/0197916 A1 * | 10/2003 | Chung | G02F 1/167 359/296 |
| 2006/0173242 A1 * | 8/2006 | Navok | A61B 1/0011 600/133 |
| 2007/0139752 A1 * | 6/2007 | Bernstein | G02B 7/1821 359/224.1 |
| 2009/0253967 A1 * | 10/2009 | Gill | A61B 1/00059 600/249 |
| 2011/0098530 A1 * | 4/2011 | Yamane | A61B 1/00172 600/109 |
| 2012/0257235 A1 * | 10/2012 | Hino | G02B 26/085 358/1.13 |
| 2013/0072855 A1 * | 3/2013 | Sherry | A61B 17/3478 604/22 |

OTHER PUBLICATIONS

Hamalainen, Matti, et al., Magnetoencephalography—theory, instrumentation, and applications to noninvasive studies of the working human brain, Reviews of modern Physics, vol. 65, No. 2 (1993).

Hari, Riitta, et al., Magnetoencephalography: From SQUIDs to neuroscience: Neuroimage 20th Anniversary Special Edition, Neuroimage, vol. 61, No. 2, pp. 386-396 (2012).

Khaligh, Alireza, et al., Kinetic Energy Harvesting Using Piezoelectric and Electromagnetic Technologies—State of the Art, IEEE Transaction on Industrial Electronics, vol. 57, No. 3, pp. 850-860 (2010).

Kim, Ki Hean, et al., In vivo 3D human vocal fold imaging with polarization sensitive optical coherence tomography and a MEMS scanning catheter, Optics Express, vol. 18, No. 14, pp. 14644-14653 (Jul. 5, 2010).

Seo, Dongjin, et al., Neural Dust: An Ultrasonic, Low Power Solution for Chronic Brain-Machine Interfaces, arXiv preprint arXiv, 1307.2196 (Jul. 8, 2013).

Wikswo, Jr., John P., et al., Magnetic Field of a Nerve Impulse: First Measurements, Science, vol. 208, No. 4439, pp. 53-55 (Apr. 4, 1980).

* cited by examiner

MICRO-MAGNETIC REPORTER AND SYSTEMS

CROSS-REFERENCE TO RELATED PATENT APPLICATIONS

This application claims priority to U.S. Provisional Patent Application 61/900,692, filed on Nov. 6, 2013, which is incorporated herein by reference in its entirety.

BACKGROUND OF THE DISCLOSURE

Various anatomical structures generate weak magnetic fields. For example, when firing, neurons generate ionic currents. As the currents flow along the length of the neurons' dendrites, the flowing current generates weak magnetic fields. Because of the small magnitude of the magnetic fields generated by anatomical structures in comparison to environmental magnetic fields it is difficult to monitor anatomically generated magnetic fields.

SUMMARY OF THE DISCLOSURE

According to one aspect of the disclosure, a system includes a magnetic reporter. The magnetic reporter includes a platform coupled to a support structure by a plurality of torsional flexures. The platform is configured to rotate about an axis. The magnetic reporter also includes a magnet disposed on the platform. The system also includes a hermetic package forming a seal around the magnetic reporter.

In some implementations, the system includes a wound coil disposed proximal to the magnetic reporter, an energy source electrically coupled with the wound coil, a controller to control a flow of current between the energy source and the wound coil, and a sensor electrically coupled to the controller and configured to measure a physiological signal.

In some implementations, the controller is configured to enable the current flow from the energy source to the wound coil responsive to detecting a signal above a predetermined threshold. The sensor can be an implantable electroencephalography electrode or an ion concentration sensor. In some implementations, the energy source is one of a capacitor and a rechargeable battery. In some implementations, the wound coil acts as an energy scavenger and recharges the energy source.

In some implementations, the plurality of torsional flexures suspend the platform over a recess in a capping layer. The plurality of torsional flexures includes at least one pair of torsional flexures coupled to opposite ends of the platform. The magnet includes a polymer binder and a magnetic powder in some implementations. A second magnet can be disposed on a second face of the platform.

According to another aspect of the disclosure, a method of measuring physiological parameters includes implanting a magnetic reporter system into a patient. The magnetic reporter system includes a magnetic reporter. The magnetic reporter includes a platform coupled to a support structure by a plurality of torsional flexures. The platform is configured to rotate about an axis. The magnetic reporter also includes a magnet disposed on the platform. The magnetic reporter system also includes a hermetical package forming a seal around the magnetic reporter. The method also includes monitoring a physiological parameter with the magnetic reporter system, and measuring a magnetic field generated by the magnetic reporter system in response to a change in the monitored physiological parameter.

In some implementations, magnetic field generated by the magnetic reporter is measured external to the patient's body. The magnetic reporter system can be implanted proximal to a neuron. In some implementations, the method includes passively amplifying a magnetic field detected by the magnetic reporter system. In some implementations, the method also includes energizing, responsive to a change in the monitored physiological parameter, the wound coil.

In some implementations, the magnetic reporter includes a wound coil disposed proximal to the magnetic reporter, an energy source electrically coupled with the wound coil, a controller to control a flow of current between the energy source and the wound coil, and a sensor electrically coupled to the controller and configured to measure a physiological signal.

In some implementations, the method includes applying an alternating magnetic field to the wound coil to induce a current in the wound coil, and then supplying the current to the energy supply. The sensor can be an implantable electroencephalography electrode or an ion concentration sensor. The energy source is one of a capacitor and a rechargeable battery in some implementations.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
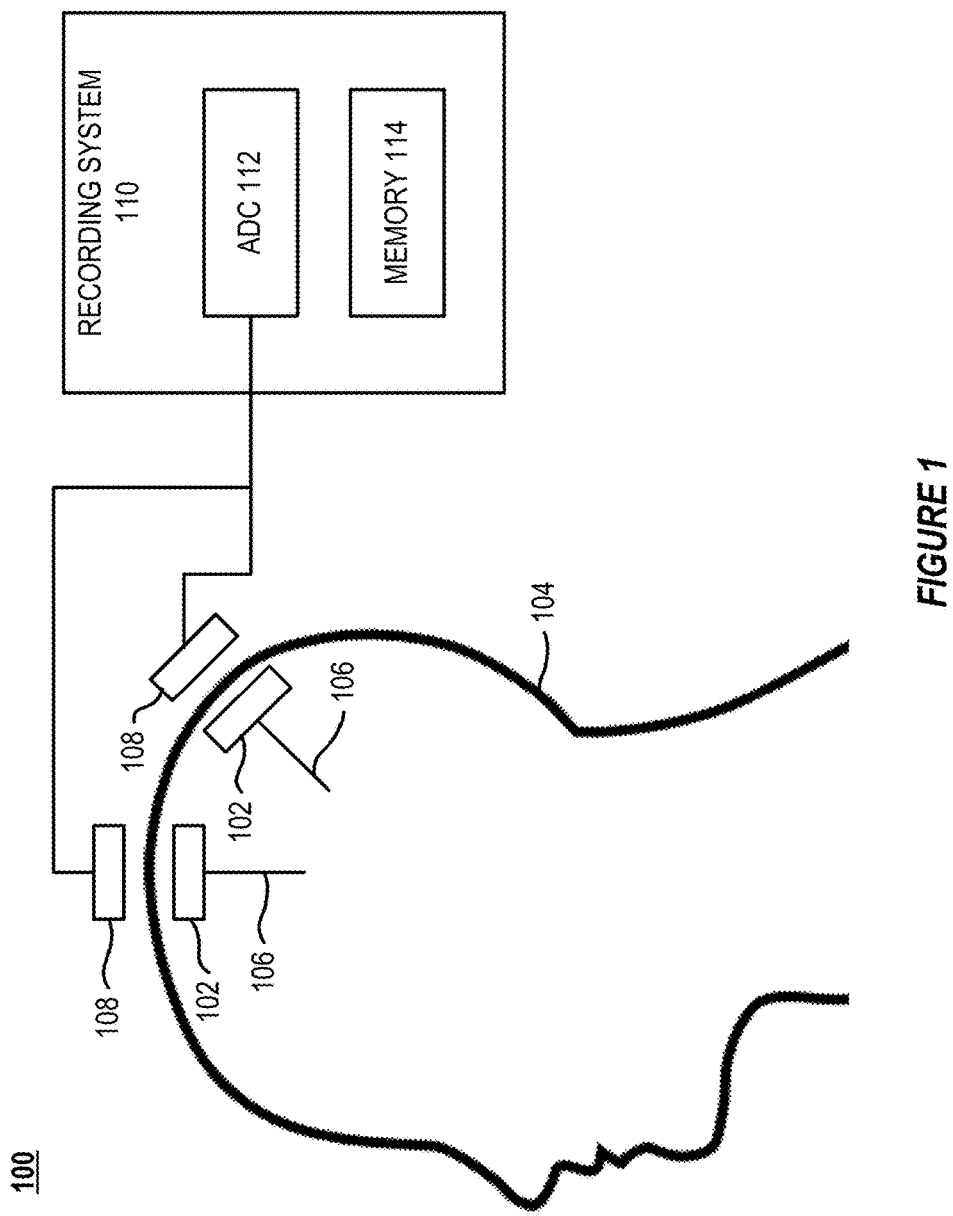
FIG. 1 illustrates an example system for measuring physiological parameters with magnetic reporters.

FIG. 1 illustrates an example system 100 for measuring physiological parameters with magnetic reporters 102. The system 100 includes magnet reporters 102 implanted into the head 104 of a patient. The system 100 includes sensors 106 coupled to each of the magnetic reporters 102 for detecting the physiological parameter to be measured. Magnetic field sensors 108 are positioned external to the magnetic reporters 102 and detect the signals (e.g., alternating magnetic fields) generated by the magnetic reporters 102. The magnetic field sensors 108 are coupled to a recording system 110. The recording system 110 includes an analog to digital converter circuit 112 that converts the signal received from the magnetic field sensors 108 into a digital signal. Responsive to be converted to a digital signal, the signal from the magnetic field sensors 108 is stored in memory 114. In some implementations, the digitized signal is displayed to a user (or patient) by a display. In some implementations, the magnetic reporter 102 is implanted elsewhere in the patient's body. For example, the magnetic reporter 102 can be implanted in the patient's thoracic cavity or in a tissue pocket formed in the chest of the patient.

Figure 2:
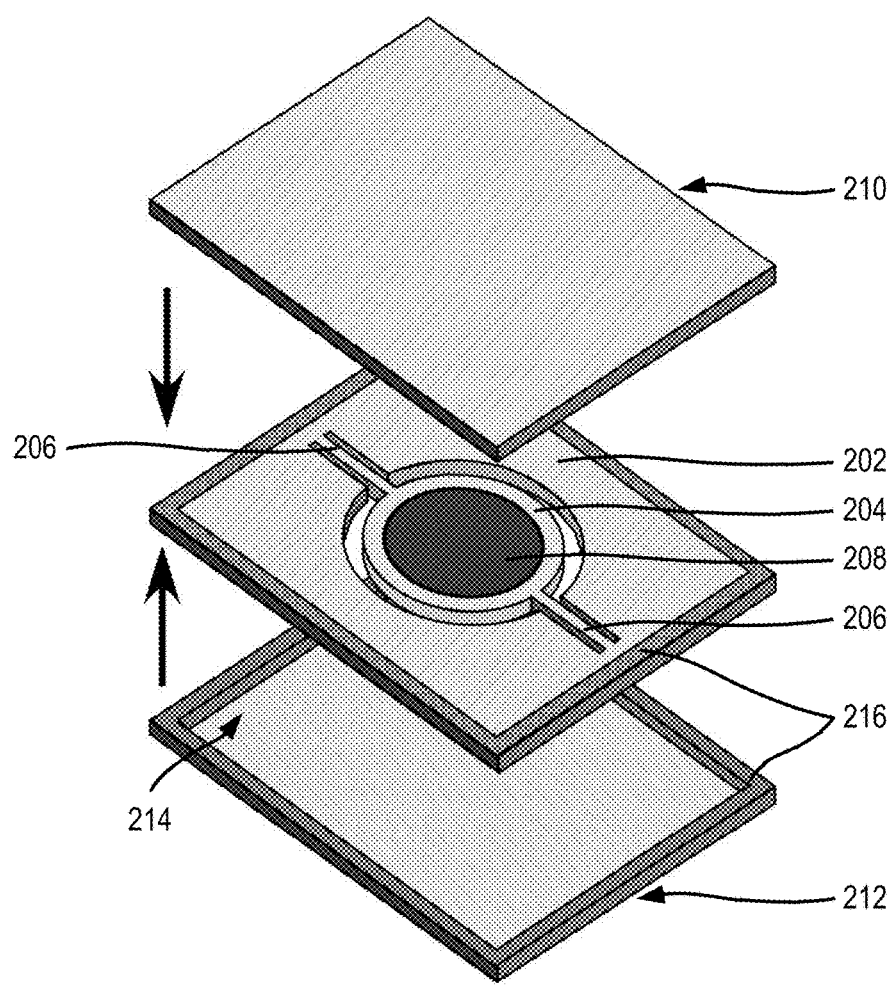
FIG. 2 illustrates an exploded view of an example passive magnetic reporter for use in the system illustrated in FIG. 1.
Figure 3:
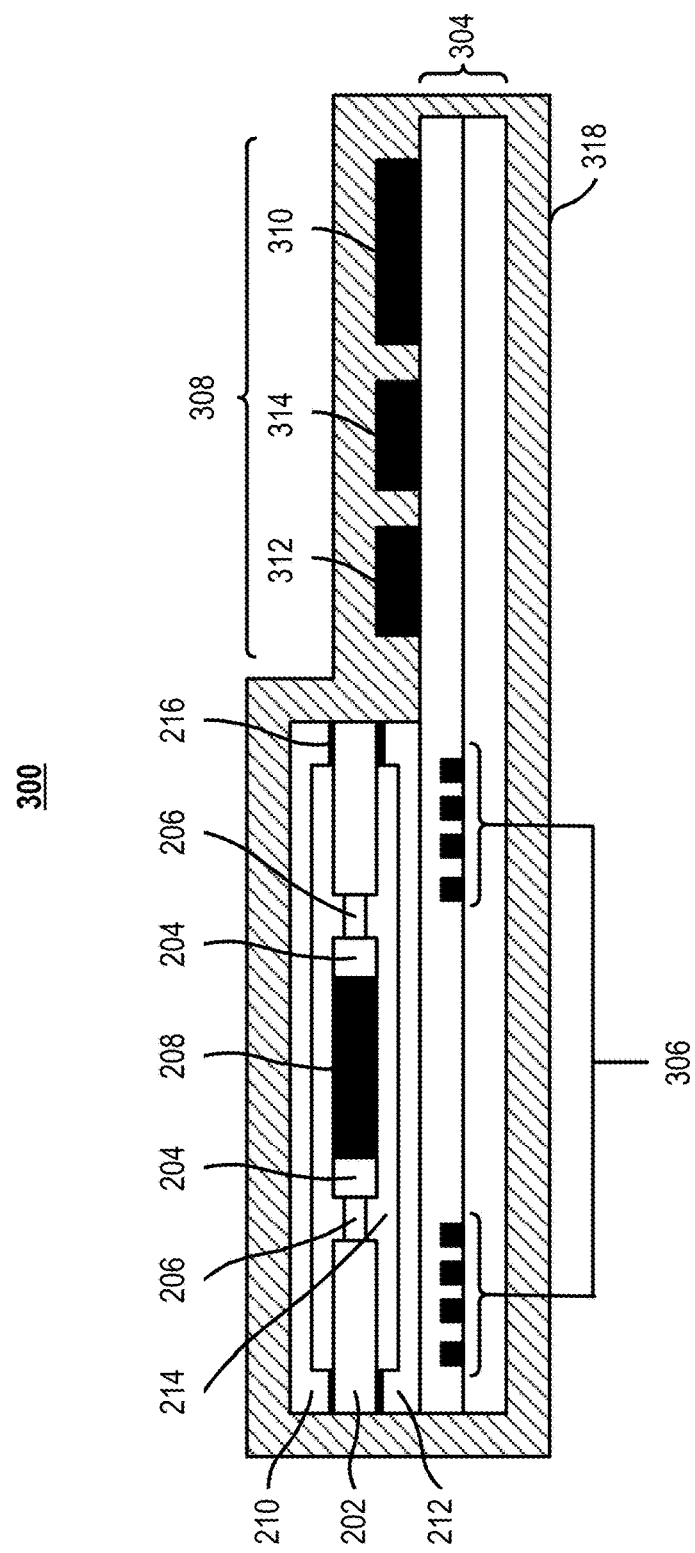
FIG. 3 illustrates a cross-sectional view of an example active magnetic reporter system for use in the system illustrated in FIG. 1.

The magnetic reporter 102 is described further in relation to FIGS. 2 and 3, but briefly, each magnetic reporter 102 includes a permanent magnet that is free to rotate within a hermetically sealed package. In some implementations, the magnetic reporter 102 includes a support structure and a platform within the hermetically sealed package. The platform is coupled to the support structure by a pair of torsional flexures. The torsional flexures suspend the platform, such that the platform is free to rotate about an axis defined by the flexures. The permanent magnet is disposed on the platform and the platform and magnet rotate when exposed to a magnetic field. For example, in the presence of a local magnetic field, the permanent magnet rotates to align with the local magnetic field. In some implementations, as described further in relation to FIG. 2, the magnetic reporter 102 is a passive system. In other implementations, as described in relation to FIG. 3, the magnetic reporter 102 is a component of an active magnetic reporter system. The active magnetic reporter system includes (as further described in relation to FIG. 3) additional components such as a controller, a coil, and a sensor. The sensor, for example an electroencephalography (EEG) electrode, monitors physiological parameters (e.g., neural activity). The controller, responsive to the signal received from the sensor, activates the coil associated with the permanent magnet. The energized coil generates a local magnetic field, to which the permanent magnet aligns. In both the active and passive versions of the magnetic reporter 102, the magnetic field generated by the movement of the permanent magnet is detected by a magnetic field sensor 108 external to the implanted magnetic reporter 102.

The sensor 106 is a sensor configured to detect or measure a physiological or other parameter. In some implementations, the sensor 106 includes one of an EEG electrode (or other sensor configured to detect electrophysiological signals), a chemical concentration sensor, a temperature sensor, and a pressure sensor. Example chemical concentration sensors can include cortisol and adrenaline sensors (or other sensors to characterize the body's response to stress), histamine sensors (or other sensors to characterize the body's response to shock), or glucose sensors.

The magnetic field sensor 108 of the system 100 is a sensor configured to measure the local magnetic field generated by the rotation of the magnetic reporter 102. In some implementations, the magnetic field sensor 108 is a magnetometer. The magnetic field sensor 108 can be configured to detect both the strength and direction of the local magnetic field. In some implementations, the magnetic field sensor 108 is a superconducting quantum interference device (SQUID). In other implementations, the magnetic field sensor 108 includes inductive pickup coils, which generate electrical current when the local magnetic field changes. The magnetic field sensor 108 can also include Hall effect magnetometers, which generate a voltage proportional to an applied local magnetic field. In some implementations, the magnetic field sensor 108 is configured to detect magnetic fields between about 10 fT and about 100 pT, or between about 1 pT and about 100 pT. In some implementations, the patient (or portion thereof) and the magnetic field sensor 108 is placed in a magnetic shield chamber to remove external magnetic fields so the magnetic field sensor 108 detects substantially only magnetic fields generated by the magnetic reporter 102.

The magnetic field sensors 108 are coupled to the recording system 110. The recording system 110 includes analog to digital converter (ADC) 112. The ADC 112 receives analog sensor data from the magnetic field sensors 108. In some implementations, the ADC 112 includes a plurality of inputs to simultaneously receive data from each of the magnetic field sensors 108. The ADC 112 has a resolution of 8, 12, 16, 32, 64, or more bits. In some implementations, the ADC 112 is a component of the magnetic field sensors 108, and the magnetic field sensors 108 transmit a digital signal to the recording system 110.

In some implementations, the recording system 110 is a general purpose processor executing computer executable instructions, which when executed carry out the functionality described herein. In other implementations, the recording system 110 includes a special purpose circuitry such as an application-specific integrated circuit (ASIC) or a field-programmable gate array (FPGA), configured specifically for carrying out the functionality described herein. The recording system 110 also includes memory 114 for the storage and retrieval of processor executable instructions and data recorded from the magnetic reporters 102. In some implementations, the memory 114 includes one or more hard drives, solid state drives, or other forms of volatile or non-volatile memory.

FIG. 2 illustrates an exploded view of an example passive magnetic reporter 200. The magnetic reporter 200 includes a device layer 202. The platform 204 and pair of flexures 206 are machined or etched into the device layer 202, and the device layer 202 is a support structure for the platform 204 and the flexures 206. A magnet 208 is disposed on (or in) the platform 204. The passive magnetic reporter 200 also includes an upper 210 and a lower 212 capping wafer. A recess 214 is fabricated into the upper 210 and the lower 212 capping wafer to form a void within the assembled magnetic reporter 200 in which the magnet 208 can rotate. Each of the upper capping wafer 210, the lower capping wafer 212, and the device layer 202 include a bonding layer 216 that is used to bond each of the layers together. As an overview, the passive magnetic reporter 200 passively (e.g., without the input of electrical energy) amplifies magnetic fields. For example, the magnetic reporter 200 can be implanted on the surface of the brain of a patient. The neural activity below the magnetic reporter 200 generates a weak magnetic field. The weak magnetic field causes the magnet 208 of the magnetic reporter 200 to rotate. The rotation of the magnet 208 generates an alternating magnetic field substantially larger than the small magnetic field generated by the neural activity. The change in the magnetic field generated by the rotation of the magnet 208 is measured by the magnetic field sensor positioned external to the patient.

In some implementations, the upper capping wafer 210, the lower capping wafer 212, and the device layer 202 are silicon wafers. The features of the upper capping wafer 210, the lower capping wafer 212, and the device layer 202 are manufactured by silicon micromachining, deep reactive ion etching, or a combination thereof. For example, a photoresist can be applied to the device layer 202. The platform 204 and the flexures 206 can then be defined by through-etching with deep reactive ion etching. In some implementations, each of the upper capping wafer 210, the lower capping wafer 212, and the device layer 202 are machined separately. When each wafer is fully machined, the wafers are aligned and bound together to form an assembled magnetic reporter 200.

In some implementations, the platform 204 is machined to receive the magnet 208. For example, the platform 204 can include a cavity substantially the same diameter as the magnet 208. The magnet 208 can then be inserted into the cavity and bound to the platform 204 with a high temperature epoxy or solder. In other implementations, the platform 204 is substantially planar and the magnet 208 is coupled to the top face of the platform 204. In some implementations, a second magnet is also coupled to the bottom face of the platform 204.

The magnet 208 of the magnetic reporter 200 is a ferrite or a rare earth magnet and is machined to form a square, rectangular, or circular shape. In some implementations, the width (or diameter) of the magnet 208 is between about 10 μm and about 1000 μm, or between about 200 μm and about 800 μm, between about 400 μm and about 800 μm, or between about 600 μm and about 800 μm. In some implementations, the height of the magnet 208 is between about 10 μm and about 1000 μm, between about 200 μm and about 800 μm, or between about 400 μm and about 600 μm. In other implementations, the magnet 208 is formed by combining a magnetic powder with a polymer binder. In some implementations, a magnet 208 formed from the combination of a polymer binder and a magnet powder is screen printed onto the platform 204. In other implementations, the magnet is formed by sputtering or electroplating a magnetic alloy onto the platform 204.

The device layer 202 of the magnetic reporter 200 also includes a pair of flexures 206. Each flexure 206 of the pair is coupled to opposite sides of the platform 204. The flexures 206 are torsional springs that enable the magnet 208 to rotate when exposed to a local magnetic field. In some implementations, the flexures 206 function as a spring-inertia-damper system. As a spring-inertia damper system, each of the flexures 206 can have a mechanical Q between about 500 and about 1000 in air and between about 1000 and about $10^6$ in a vacuum. In some implementations, the magnetic reporter 200 is most responsive (e.g., the greatest amount of rotation of the magnet 208 occurs) when the local, alternating magnetic field the magnetic reporter 200 is exposed to is at or near a resonant frequency of the platform 204, magnet 208 and flexures 206. The DC responsiveness (e.g., the responsiveness of the magnetic reporter 200 when exposed to a constant magnetic field) of the magnetic reporter 200 is inversely proportional to the square of the magnetic reporter's resonant frequency. In some implementations, the resonant frequency of the magnetic reporter 200 is between about 50 Hz and about 500 Hz, between about 50 Hz and about 400 Hz, or between about 100 Hz and about 300 Hz. In some implementations, flexure cross-sectional height and width are between about 1 and about 1000 μm, between about 10 μm and about 1000 μm, between about 200 μm and about 800 μm, or between about 400 μm and about 600 μm. In some implementations, the flexures 206 include folded flexures, which may result in flexures with reduced spring constants when compared to beam flexures 206 (as illustrated in FIG. 2).

The upper capping wafer 210, the lower capping wafer 212, and the device layer 202 of the magnetic reporter 200 each include a patterned bond layer 216. The bond layer 216 is disposed toward the periphery of each of the upper capping wafer 210, the lower capping wafer 212, and the device layer 202. To assemble the magnetic reporter 200, the bond layers 216 of each of the layers are aligned and bound together. For example, the bond layers 216 can include Cr—Cu or Cr—Au. The bond layers 216 may be welded together through thermocompression bonding. In another example, the bond layers 216 can include Au—Sn or Al—Ge, enabling each of the bond layers 216 to be soldered together or bonded by transient liquid phase bonding (TLP). In some implementations, the upper capping wafer 210, the lower capping wafer 212, and the device layer 202 of the magnetic reporter 200 are bound together under a vacuum as to form a vacuum within the void of the magnetic reporter 200.

FIG. 3 illustrates a cross-sectional view of an example active magnetic reporter system 300. The active magnetic reporter system 300 includes magnetic reporter 320 similar to the passive magnetic reporter 200 described in relation to FIG. 2. As described above in relation to FIG. 2, the magnetic reporter 320 includes a lower capping wafer 212, an upper capping wafer 210, and a device layer 202. Flexures 206 couple the platform 204 and magnet 208 to the support structure of the device layer 202. The platform 204 and the magnet 208 are suspended above a recess 214 formed in the lower capping wafer 212. The magnetic reporter 320 is coupled to a printed circuit board or flexboard (generally referred to as a PCB 304). The PCB 304 includes an inductive coil 306 formed in a metal layer. The inductive coil 306 is electrically coupled to a control circuit 308 that includes a controller 310, an amplifier 312, and an energy source 314. A signal generated by a sensor 316 is received as an input by the control circuit 308.

The active magnetic reporter system 300 includes an inductive coil 306 within the PCB 304. In some implementations, the inductive coil 306 is defined in a metal layer within the PCB 304 and includes a predetermined number of loops. In some implementations, the magnetic reporter 320 is coupled to the PCB 304 above the inductive coil 306. When energized by the energy source 314, the inductive coil 306 generates a local magnetic field, which in turn rotates the magnet 208. The rotating magnet 208 generates a larger magnetic field, which is detectable by a magnetic field sensor external to the patient. In some implementations, the inductive coil 306 is defined in the device layer 202 rather than in the PCB 304. In some implementations, the inductive coil 306 also acts as an energy scavenger and scavenges energy to charge the energy source 314. For example, when the energy source 314 reaches a predetermined energy level (or at predetermined intervals) an alternating magnetic field can be applied external to the implantation site. The alternating magnetic field causes the magnet 208 to rotate, which generates a current in the inductive coil 306. The current generated by the inductive coil 306 is provided to the energy source 314 of the control circuit 308. In some implementations, when acting in an energy scavenging capacity, the inductive coil 306 generates between about 1 V and about 3 V. The voltage generated by the inductive coil 306 is proportional to the number of loops in the inductive coil 306 or the total length of the inductive coil 306.

The control circuit 308 of the active magnetic reporter system 300 includes a controller 310. In some implementations, the controller 310 is an ASIC controller. The controller 310 is configured to monitor the signal generated by the sensor 316. The sensor 316 can be any of the sensors 106 described above in relation to FIG. 1. In some implementations, the controller 310 monitors the signal generated by the sensor 316 and determines when the signal crosses a predetermined threshold. For example, the sensor 316 can include an EEG depth electrode. When a neuron firing is detected by the EEG depth electrode, the controller 310 can energize the inductive coil 306 with current supplied from the energy source 314. In some implementations, the energy source 314 is a thin-film battery, a lithium ion battery, or a capacitor.

When assembled, the active magnetic reporter system 300 is encapsulated by an encapsulating layer 318. The encapsulating layer 318 is a biocompatible material, and reduces the patient's immune response when the active magnetic reporter system 300 is implanted. The encapsulating layer 318 also protects the components of the active magnetic reporter system 300. The encapsulating layer 318 includes biocompatible materials such as titanium, ceramics, metals, polymers, silicon, or other materials used in the housing of implantable devices. In some implementations, the encapsulating layer 318 is deposited on the active magnetic reporter system 300 using a thin film deposition technique such as sputtering, atomic layer deposition, or similar techniques. In some implementations, coatings can be applied to the encapsulating layer 318. For example, a protein layer or drug eluting layer can be applied the exterior of the encapsulating to further reduce the patient's immune response to the implanted active magnetic reporter system 300.

Figure 4:
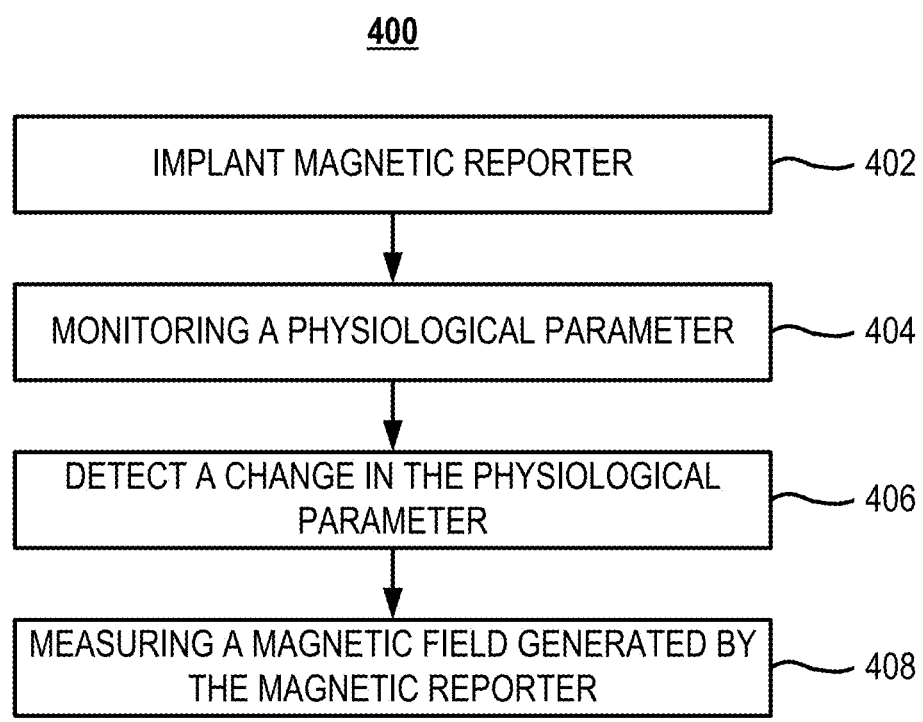
FIG. 4 illustrates an example method of monitoring a physiological condition using the system illustrated in FIG. 1.

FIG. 4 illustrates an example method 400 of monitoring physiological conditions. The method 400 includes implanting a magnetic reporter (step 402). A physiological parameter is then monitored (step 404), and a change in the physiological parameter is detected (step 406). A magnetic field generated by the magnetic reporter in response to the detected change in the physiological parameter is then measured (step 408).

As set forth above, the method 400 includes implanting a magnetic reporter (step 402). In some implementations, the implanted magnetic reporter is a passive magnetic reporter as described in relation to FIG. 2, and in other implementations the implanted magnetic reporter is an active magnetic reporter system as described in relation to FIG. 3. The magnetic reporter is implanted near the anatomical structure generating the physiological parameter to be measured. For example, to measure neural activity of the brain, the magnetic reporter may be implanted beneath the scalp of the patient. In some implementations, the magnetic reporter is configured to detect electrophysiology signals such as signals generated by the vagus nerve, the brain, peripheral nerves, the heart, or a combination thereof. The magnetic reporter can also be implanted in other locations throughout the body to measure temperature, chemical concentrations, or pressures. Referring again to FIG. 1, in some implementations the magnetic reporter includes a sensor 106. In some of these implementations, the sensor 106 is implanted near the anatomical structure to be monitored and the magnetic reporter is implanted in a secondary location. For example, to monitor the vagus nerve, a sensor 106 may be disposed on or near the vagus nerve and the magnetic reporter may be implanted in a tissue pocket formed by a small incision in the patient's skin.

After implantation, a physiological parameter is monitored (step 404). For an active magnetic reporter system, a controller in the system monitors a signal generated by the sensor. For example, the sensor may be an EEG electrode monitoring neural activity in a patient's brain, an electrode measuring the activity of the vagus nerve, or a chemical concentration sensor measuring the concentration of a predetermined chemical in the patient's blood stream. In some implementations, a passive magnetic reporter does not include a sensor and is placed in proximity to the anatomical structure to be monitored (e.g., a neuron, brain, or vagus nerve). As a passive device, the passive magnetic reporter may not generate a response until a signal (e.g., neural firing that generates a weak magnetic field) is detected in or near the resonate frequency of the passive magnetic reporter.

The method 400 also includes detecting a change in the physiological parameter (step 406). In some implementations of an active magnetic reporter system, the change in the physiological parameter is detected when the physiological parameter crosses a threshold. For example, the active magnetic reporter system can monitor neural activity. In this example, the active magnetic reporter system detects a neuron firing by detecting that the electrophysiological signal from an EEG sensor crossed a predetermined threshold. In implementations with a passive magnetic reporter, the passive magnetic reporter detects a weak magnetic field when the frequency of the alternating weak magnetic field is in or near the resonant frequency of the passive magnetic reporter. In response to the weak alternating magnetic field, the magnet of the passive magnetic reporter rotates to generate a stronger magnetic field.

A magnetic field generated by the magnetic reporter is detected (step 408). In some implementations, the magnetic field is detected by a magnetic field sensor located external to the patient. For a passive magnetic reporter, the magnet of the passive magnetic reporter rotates to align with the magnetic field created by, for example, the electrical currents created by the firing of neurons. The weak magnetic field created by the neurons may not be sufficiently strong to be reliably detected by the magnetic field sensor located outside the patient; however, the weak magnetic field is strong enough to cause the magnet within the magnetic reporter to rotate. The rotation of the magnet within the magnetic reporter generates a stronger, alternating magnetic field, which is detectable by the magnetic field sensor located external to the patient. By passively generating a stronger magnetic field that corresponds to the weaker magnetic field generated by the firing neurons, the magnetic reporter passively amplifies the weak magnetic field.

For an active magnetic reporter system, the magnetic field detected in step 408 is generated when the controller detects a signal from the sensor crosses a predetermined threshold. Responsive to the crossing of the predetermined threshold, the controller can pulse energy through the coil of the active magnetic reporter system. The flow of current through the coil generates a magnetic field, to which the magnet of the magnetic reporter aligns. The magnetic field sensor external to the patient detects the change in the magnetic field generated by the rotation of the magnet of the active magnetic reporter system. In some implementations, rather than only energizing the coil when a threshold crossing is detected, the controller can continually modulate the amount of current flowed through the coil. In these implementations, the magnet of the active magnetic reporter system rotates responsive to the magnitude of the signal received by the controller from the sensor, which can enable a continuous representation of the measured physiological parameter to be detected by the magnetic field sensor.

In some implementations when an active magnetic reporter system is used in the method 400, the method 400 also includes charging and energy source of the active magnetic reporter system. In some implementations, the coil of the active magnetic reporter system is used as an energy scavenger. When employed as an energy scavenger, an alternating magnetic field is applied proximal to the active magnetic reporter system, but external to the patient. For example, the patient with an implanted active magnetic reporter system may wear a charging helmet at predetermined intervals. The charging helmet may include one or more induction coils through which current is flowed to create an alternating magnetic field. Through inductive coupling, the alternating magnetic field generates a current within the coil of the active magnetic reporter system, which is provided back to the energy source to charge the energy source.

The disclosed system and methods may be embodied in other specific forms without departing from the spirit or essential characteristics thereof. The forgoing implementations are therefore to be considered in all respects illustrative, rather than limiting of the invention.

What is claimed:

1. A system comprising:
    a magnetic reporter comprising:
        a platform coupled to a support structure by a plurality of torsional flexures, wherein the platform is configured to rotate about an axis; and
        a magnet disposed on the platform;
    a wound coil disposed proximal to the magnetic reporter;
    an energy source electrically coupled with the wound coil;
    a sensor configured to measure a physiological signal;
    a controller electrically coupled to the sensor and configured to control a flow of current between the energy source and the wound coil based on the measured physiological signal; and
    a hermetical package forming a seal around the magnetic reporter.

2. The system of claim 1, wherein the controller is configured to enable the current flow from the energy source to the wound coil responsive to detecting a signal above a predetermined threshold.

3. The system of claim 1, wherein the sensor is an implantable electroencephalography electrode.

4. The system of claim 1, wherein the sensor is an ion concentration sensor.

5. The system of claim 1, wherein the energy source is one of a capacitor and a rechargeable battery.

6. The system of claim 1, wherein the wound coil is an energy scavenger configured to recharge the energy source.

7. The system of claim 1, wherein the plurality of torsional flexures suspend the platform over a recess in a capping layer.

8. The system of claim 1, wherein the plurality of torsional flexures comprises at least one pair of torsional flexures coupled to opposite ends of the platform.

9. The system of claim 1, wherein the magnet comprises a polymer binder and a magnetic powder.

10. The system of claim 1, further comprising a second magnet disposed on a second face of the platform.

11. A method comprising:
    implanting a magnetic reporter system in a patient, the magnetic reporter system comprising:
        a magnetic reporter comprising a platform coupled to a support structure by a plurality of torsional flexures, wherein the platform is configured to rotate about an axis; and a magnet disposed on the platform;
        a wound coil disposed proximal to the magnetic reporter;
        an energy source electrically coupled with the wound coil;
        a controller to control a flow of current between the energy source and the wound coil;
        a sensor electrically coupled to the controller and configured to measure a physiological signal; and
        a hermetical package forming a seal around the magnetic reporter;
    monitoring a physiological parameter with the magnetic reporter system;
    measuring a magnetic field generated by the magnetic reporter system in response to a change in the monitored physiological parameter.

12. The method of claim 11, further comprising measuring the magnetic field generated by the magnetic reporter with a magnetic field sensor external to the patient.

13. The method of claim 11, further comprising implanting the magnetic reporter system proximal to a neuron.

14. The method of claim 11, further comprising energizing, responsive to a change in the monitored physiological parameter, the wound coil.

15. The method of claim 11, further comprising:
    applying an alternating magnetic field to the wound coil to induce a current in the wound coil; and
    supplying the current to the energy source.

16. The method of claim 11, wherein the sensor is one of an implantable electroencephalography electrode and an ion concentration sensor.

17. The method of claim 11, wherein the energy source is one of a capacitor and a rechargeable battery.

* * * * *